United States Patent
Zander et al.

(10) Patent No.: US 10,828,073 B2
(45) Date of Patent: Nov. 10, 2020

(54) EXPANDABLE BONE NAIL

(71) Applicant: Stryker European Holdings I, LLC, Kalamazoo, MI (US)

(72) Inventors: Nils Zander, Eckernförde (DE); Lars Metz, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 25 days.

(21) Appl. No.: 15/778,097

(22) PCT Filed: Dec. 17, 2015

(86) PCT No.: PCT/IB2015/059720
§ 371 (c)(1),
(2) Date: May 22, 2018

(87) PCT Pub. No.: WO2017/103658
PCT Pub. Date: Jun. 22, 2017

(65) Prior Publication Data
US 2018/0353226 A1    Dec. 13, 2018

(51) Int. Cl.
*A61B 17/72* (2006.01)

(52) U.S. Cl.
CPC ...... *A61B 17/7258* (2013.01); *A61B 17/7266* (2013.01)

(58) Field of Classification Search
CPC ........... A61B 17/72–7291; A61B 17/844–846; A61B 17/74–748
See application file for complete search history.

(56) References Cited

U.S. PATENT DOCUMENTS

| | | | | |
|---|---|---|---|---|
| 2,381,050 | A * | 8/1945 | Hardinge | A61B 17/742 606/65 |
| 4,204,531 | A * | 5/1980 | Aginsky | A61B 17/7225 606/63 |
| 4,590,930 | A * | 5/1986 | Kurth | A61B 17/7258 606/63 |
| 5,032,133 | A * | 7/1991 | Carbone | A61B 17/7258 623/23.26 |
| 5,057,103 | A * | 10/1991 | Davis | A61B 17/7225 606/63 |
| 5,458,599 | A * | 10/1995 | Adobbati | A61B 17/7225 606/54 |
| 5,814,047 | A * | 9/1998 | Emilio | A61B 17/7266 606/302 |
| 6,443,954 | B1 * | 9/2002 | Bramlet | A61B 17/744 606/304 |

(Continued)

OTHER PUBLICATIONS

International Search Report for Application No. PCT/IB2015/059720 dated Sep. 5, 2016, 4 pages.

*Primary Examiner* — Eduardo C Robert
*Assistant Examiner* — Michelle C Eckman
(74) *Attorney, Agent, or Firm* — Lerner, David, Littenberg, Krumholz & Mentlik, LLP

(57) ABSTRACT

An intramedullary nail is suggested comprising a nail shaft with a lateral recess, with an expansion element being arranged in that recess, and an adjustment screw for adjusting the position and orientation of the expansion element relative to the nail shaft. A threaded bore may be formed in the nail shaft, wherein the threaded bore extends through the nail shaft and into the recess and is adapted to receive the adjustment screw.

13 Claims, 2 Drawing Sheets

(56) References Cited

U.S. PATENT DOCUMENTS

| | | | | |
|---|---|---|---|---|
| 9,974,581 | B2* | 5/2018 | Jansen | A61B 17/7275 |
| 2010/0152786 | A1* | 6/2010 | Behrbalk | A61B 17/68 |
| | | | | 606/301 |
| 2011/0306975 | A1* | 12/2011 | Kaikkonen | A61B 17/7097 |
| | | | | 606/63 |
| 2013/0046307 | A1* | 2/2013 | Yang | A61B 17/744 |
| | | | | 606/64 |
| 2013/0116693 | A1* | 5/2013 | Nelson | A61B 17/7233 |
| | | | | 606/64 |
| 2014/0121709 | A1* | 5/2014 | Gonzalez-Hernandez | |
| | | | | A61F 2/4261 |
| | | | | 606/286 |
| 2016/0089189 | A1* | 3/2016 | Buscaglia | A61B 17/1725 |
| | | | | 606/64 |
| 2017/0143387 | A1* | 5/2017 | Jansen | A61B 17/7216 |
| 2017/0143390 | A1* | 5/2017 | Jansen | A61B 17/744 |
| 2017/0143391 | A1* | 5/2017 | Jansen | A61B 17/7216 |
| 2018/0092674 | A1* | 4/2018 | McDaniel | A61B 17/1775 |
| 2018/0344366 | A1* | 12/2018 | Wodajo | A61B 17/8004 |
| 2019/0201061 | A1* | 7/2019 | Tsai | A61B 17/7266 |

\* cited by examiner

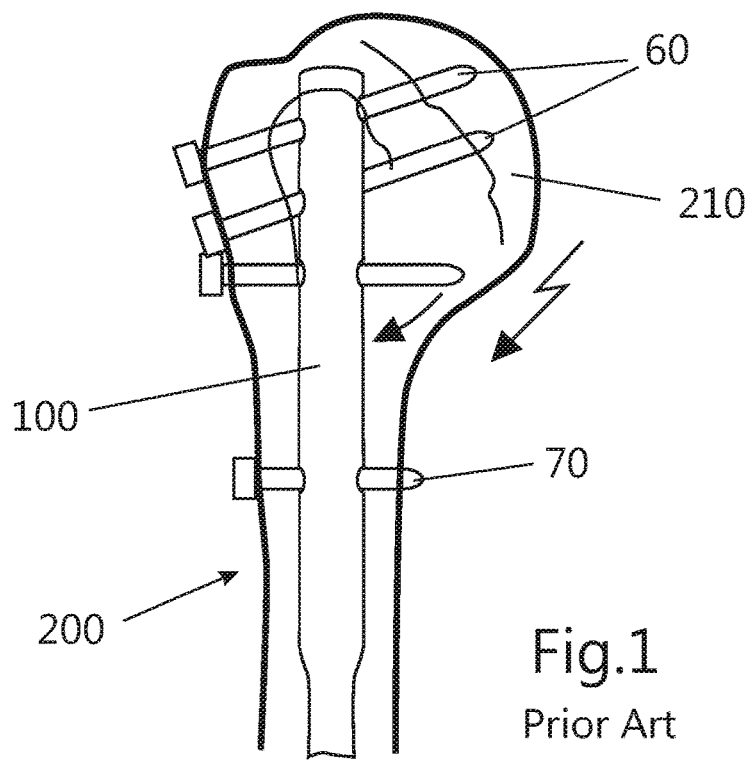
Fig.1
Prior Art
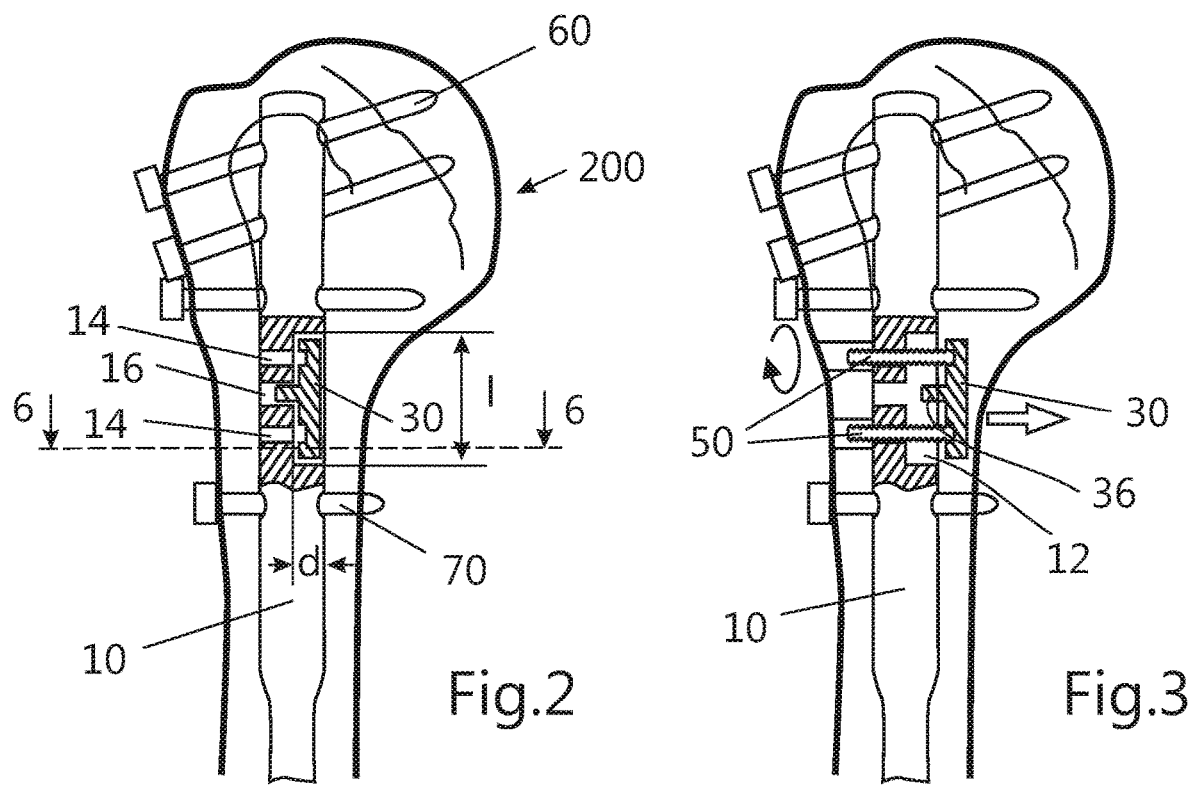
Fig.2
Fig.3

EXPANDABLE BONE NAIL

CROSS-REFERENCE TO RELATED APPLICATIONS

The present application is a national phase entry under 35 U.S.C. § 371 of International Application No. PCT/IB2015/059720, filed Dec. 17, 2015, the disclosure of which is hereby incorporated herein by reference.

FIELD OF THE DISCLOSURE

The invention relates to an implant. In particular, the invention relates to a bone nail the size of which can be expanded in a transverse direction.

BACKGROUND INFORMATION

An implant and particularly a bone implant include a portion or section or end which is adapted to be firstly introduced into a body during an implantation. Such a portion or section or end is usually referred to as leading portion or leading section or leading end. Consequently, an opposite portion or section or end of the implant is adapted to be finally introduced, wherein this portion or section or end may additionally be configured for an engagement of a tool for inserting the implant into the body. Such a portion or section or end is usually referred to as trailing portion or trailing section or trailing end.

A bone implant may be a pin or a nail. A bone nail may be an intramedullary nail, for example a femur nail, a humerus nail or a tibia nail. A bone screw may be a screw for fixing fragments of a bone fracture or may be a locking screw for locking a bone nail in the bone.

The trailing end of the implant may further act as an interface towards a target or aiming device.

A bone, in particular a long bone like the femur, tibia or humerus comprises a corticalis formed by a harder material which forms an outer surface and a few millimeters of a wall structure of the bone, and a spongious material inside the bone forming a so called marrow channel. A bone nail is usually inserted through the corticalis and into the marrow channel. However, it may occur that the space in the marrow channel is wider than the cross section of the bone nail so that the bone nail may shift inside the bone, or at least a bone fragment may move relative to the bone nail as well as relative to other fragments.

FIG. 1 show an example of a situation which may occur with a bone nail according to the prior art. The bone nail 100 is located in a proximal portion of a humerus bone 200. However, the area with spongious material inside the proximal portion of the humerus bone widens as the bone contour widens at the joint head 210 of the humerus. Assuming that the humerus bone is fractured so that the joint head is broken into a plurality of fragments, bone screws 60, 70 are inserted through the bone nail so as to hold the fragments in natural positions and to allow the fragment to grow together. However, the position and orientation of the fragment relative to each other may change when the bone nail is displaced inside the spongious material. Fragments may move as indicated by the arrows in FIG. 1.

SUMMARY OF THE INVENTION

An object may be to provide an implant, in particular an intramedullary nail being adapted to better stabilize fracture fragments of a bone relative to the implant.

This is achieved by the subject matter according to the independent claims. Further embodiments are described in the dependent claims.

In general, an intramedullary nail in accordance with an embodiment comprises a nail shaft with a lateral or side recess, with an expansion element being arranged in that recess, and an adjustment screw for adjusting the position and orientation of the expansion element relative to the nail shaft. The adjustment screw may be directly or indirectly engagable with the expansion element.

The shaft comprises a central longitudinal axis, an outer surface extending in a longitudinal direction and in a circumferential direction, wherein the recess is formed in the outer surface of the nail shaft. The recess has a length measured in the longitudinal direction, a width measured in a circumferential direction and a depth measured from the outer surface of the shaft in a direction to the central longitudinal axis. Furthermore, a threaded bore may be formed in the nail shaft, the threaded bore extending through the nail shaft and into the recess.

The expansion element is formed with a shape and size which fits to the recess. At least, the expansion element is adapted to be accommodated in the recess. To allow an adjustment of the distance between the central longitudinal axis of the nail shaft and the expansion element, the adjustment screw may be accommodated in the threaded bore and may be arranged so as to be in contact with the expansion element. A turning of the adjustment screw may cause a translation of the screw in the threaded bore and such a translational movement may cause a shifting of the expansion element laterally away from the nail shaft.

According to an embodiment, the adjustment screw may further be adapted to adjust an angle between the central longitudinal axis of the nail shaft and the expansion element. For example, the movement of the expansion element may be guided along a curved line and/or may be hinged so as to rotate about a hinge axis.

According to an embodiment, the adjustment screw may further be adapted to adjust a bending of the expansion element. It will be understood that the expansion element may be elastically deformable and/or plastically deformable. For example, the expansion element may be fixedly connected to the nail shaft at an end of the expansion element and a force is applied to the expansion element causing a bending along the extend of the expansion element in a cantilever fashion. In a case in which the end of the expansion element which is arranged in the longitudinal direction is fixedly connected to the nail shaft, the bending will substantially occur along a longitudinal extend of the expansion element.

According to a further embodiment, the intramedullary nail may comprise at least one and preferably two threaded bores extending through the nail shaft and into the recess, and two adjustment screws. Two adjustment screws allow an application of a higher force and/or allow an adjustment of the distance as well as of the angle relative to the longitudinal axis of the nail shaft. It will be understood that also more than two adjustment screw may be provided to achieve these effects.

According to another embodiment, the nail shaft of the intramedullary nail may further comprise a first guiding means and the expansion element may further comprises a second guiding means, wherein the first and second guiding means are adapted to engage each other and to guide an adjustment movement of the expansion element relative to the nail shaft. Such a guiding structure may be realized by a kind of a guiding rail realized by a dovetail or tongue and groove engagement, and giving a predetermined movement of the expansion element along that guiding rail, for example firstly along a straight path and then along a curved path. It will be understood that a guiding structure may be adapted to the particular bone nail, depending on the intended implantation site.

According to an embodiment, the length of the recess may be between 10 mm and 40 mm, preferably between 20 mm and 25 mm, the width of the recess may be between 1 mm and 8 mm, preferably between 2 mm and 5 mm, and the depth of the recess may be up to 2 mm, preferably up to 1 mm. Such dimensions may be provided at a nail shaft having a diameter of about 10 mm.

According to a further embodiment, the shape and size of the expansion element may be determined such that a contour of the outer surface of the nail shaft at the recess is completed by the expansion element, when the expansion element is accommodated in the recess. In other words, the recess in the outer surface of the nail shaft may be mainly filled by the expansion element and an outer surface of the expansion element may be flush with the surrounding outer surface of the nail shaft, so that the outer surface of the nail shaft together with the outer surface of the expansion element provide a smooth outer surface for insertion of the bone nail into a marrow channel of a bone. After the insertion, the expansion element may be pushed out of the recess by means of the adjustment screw until the outer surface of the expansion element abuts the corticalis of the bone for stabilizing the position and orientation of the nail in the bone.

It is noted that the cross section of the nail shaft may have any suitable shape. For example, the cross section of the nail shaft may be circular or non-circular, wherein a non-circular cross section may be oval, barbell-shaped or constricted, square or rectangular, with or without rounded edges, or may have any other arbitrary contour. Furthermore, the cross section of the nail may vary along the length of the nail.

An exemplary bone nail may be an intramedullary nail further comprising at least one through bore for receiving a locking screw, the through bore extending through the shaft of the bone nail in a direction transverse and possibly also inclined relative to a longitudinal axis of the shaft. By means of such locking screws, bone fragments may be fixed in position relative to the nail shaft stabilized in the bone.

The intramedullary nail may further comprise a bore formed at least in the trailing end section of the nail, with the bore extending in a longitudinal direction of the shaft of the nail, the longitudinal bore including an inner thread for releasably fixing a medical device like a driving tool for manipulating the implant during an implantation or like a targeting device, wherein the inner thread is also adapted to receive an end cap.

As already indicated above, an intramedullary nail may initially be provided with the expansion element being arranged within the recess of the nail shaft, thus forming a smooth outer surface for insertion. The nail may then be inserted through hard material of a corticalis of a long bone and into the marrow channel having softer spongious material. When placed in the bone at an intended position and orientation, the adjustment screw may be operated, e.g. screwed in, so that the expansion element is moved out of the recess of the nail shaft. By expanding the overall diameter of the bone nail, i.e. the size of the bone nail in a transverse direction, the bone nail can be better supported by the harder material of the corticalis.

It has to be noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

FIG. 1 is an illustration of a bone nail according to the prior art within a humerus bone.

FIG. 2 is an illustration of a bone nail according to a first embodiment within a humerus bone, the bone nail being in a first state.

FIG. 3 is an illustration of the bone nail according to the first embodiment within a humerus bone, the bone nail being in a second state.

Figure 4:
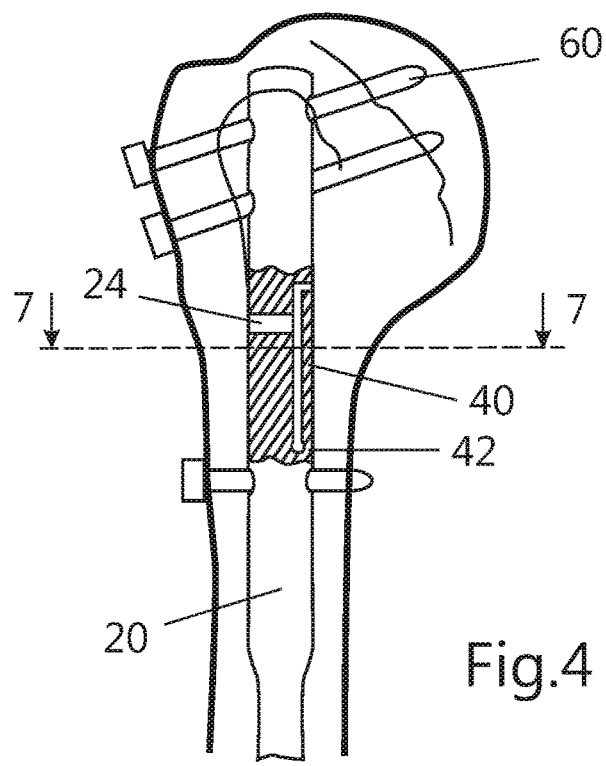
FIG. 4 is an illustration of a bone nail according to a second embodiment within a humerus bone, the bone nail being in a first state.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION OF EXEMPLARY EMBODIMENTS

FIGS. 2 and 3 are partially sectioned views of a humerus nail 10 according to a first embodiment. The nail 10 is located in a proximal portion of a humerus bone 200. The nail comprises through bores for accommodating locking screws 60 and 70. In a portion of the nail between the locking holes for the locking screws 60 in the most proximal portion of the nail and a locking hole for the screw 70 which is arranged more distally, a section of the nail 10 is provided with a lateral recess 12 in which an expansion element 30 is arranged. The recess 12 is arranged at a medial side of the humerus nail.

The recess is formed with a depth d (indicated in FIG. 2) and a length l (indicated in FIG. 3). Further, threaded bores 14 are formed through the nail. The threaded bores extend from the bottom of the recess through the nail and out of the opposite side surface of the nail. Dependent on the point of view, one may also consider the threaded bores 14 as being formed from the back side through the nail 10 and into the recess 12. Adjustment screws 50 are adapted to engage the threads in the threaded bores 14. The adjustment screws 50 can be screwed into the threaded bores 14 until the leading end of the adjustment screw abuts the expansion element 30. Further movement of the adjustment screws 50 (c.f. curved arrow in FIG. 3) cause the expansion element to move out of the recess 12 (c.f. straight arrow in FIG. 3). The length of the adjustment screws may be determined so that the expansion element may come in contact with the harder material of the corticalis, thereby supporting and/or stabilizing the nail within the marrow channel of the bone.

Furthermore, the nail may comprise a first guiding means 16 and the expansion element 30 may comprise a second guiding means 36. In the embodiment of FIGS. 2 and 3, the first guiding means 16 is a channel through the nail and the second guiding means 30 is a pin formed on a side of the expansion element 30. Although the second guiding means 36 is illustrated in the figures to be short so that the guiding means 16 and 36 disengage upon the movement of the expansion element away from the nail, it will be understood that the guiding means may have other sizes and shapes allowing a guidance of the movement of the expansion element 30 over the complete way of movement.

Figure 5:
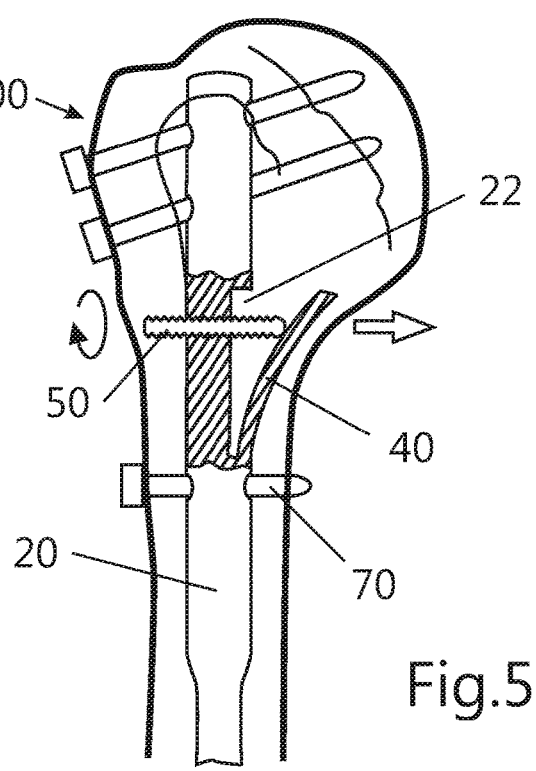
FIG. 5 is an illustration of the bone nail according to the second embodiment within a humerus bone, the bone nail being in a second state.

FIGS. 4 and 5 illustrate another embodiment of an expandable bone nail. The nail 20 is comparable with the bone nail 10 of FIGS. 2 and 3. The nail 20 also comprises through bores for receiving locking screws 60 and 70, and a recess 22 for accommodating an expansion element, wherein an adjustment screw 50 engages threads in a through bore 24 so as to allow an adjustment of the displacement of the expansion element 40.

The nail 20 differs from the nail 10 in that the expansion element 40 is fixedly connected to the nail shaft, at an end 42 of the expansion element. It will be understood that the connection between the expansion element 40 and the nail 20 may be formed as a film hinge with a thin material bridging at the end 42 from the expansion element to the nail, so that a substantially stiff expansion element may pivot about the axis of the film hinge. Alternatively, the connection between the expansion element 40 and the nail may be thick enough to cause a resistance against a rotational movement of the expansion element. In such a case, the expansion element will be bent by an operation of the adjustment screw, as illustrated in the embodiment shown in FIG. 5.

Figure 6:
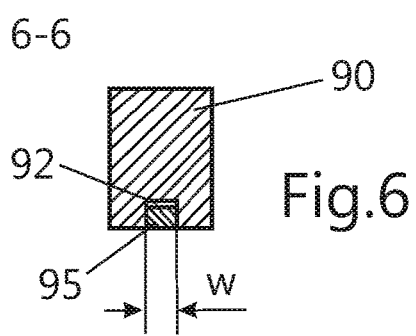
FIG. 6 is a cross section of a bone nail according to a third embodiment.
Figure 7:
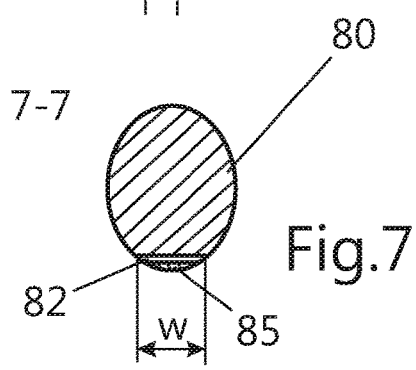
FIG. 7 is a cross section of a bone nail according to a fourth embodiment.

FIGS. 6 and 7 show cross sectional views cut through the nail shaft at the level of the recess in a transverse direction. These figures illustrate that the shape of the cross section may have different forms. Furthermore, these figures show that the recess may have different widths w.

In the embodiment of FIG. 6, the nail 90 has a rectangular cross section (along section line 6-6 in FIG. 2), with the recess 92 being formed as a groove in one side of the nail shaft. The expansion element 95 may have the shape and size complementary to the groove, like a tongue with a clearance fit. Here, the groove, i.e. the recess 92 may have a smaller width w.

In the embodiment of FIG. 7, the nail 80 has an oval cross section (along section line 7-7 in FIG. 4), with the recess 82 being cut along a secant. The expansion element 85 has a rounded outer surface substantially filling the gap in the nail shaft caused by the recess. Cutting the recess along a secant in a more or less round nail shaft results in a width w of the recess and consequently in a possible width of the expansion element.

Figure 8:
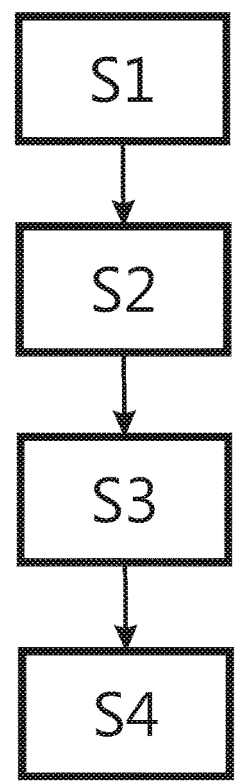
FIG. 8 is a flow chart illustrating steps of a method of using the bone nail.

The flow-chart in FIG. 8 illustrates the principle of the steps performed when using the above described bone nail. It will be understood that the steps described, are major steps, wherein these major steps might be differentiated or divided into several sub-steps. Furthermore, there might be also sub-steps between these major steps.

In step S1, a bone nail is provided, the bone nail having a lateral recess and an expansion element being arranged in the recess so that the expansion element does not protrude beyond the outer surface of the nail shaft surrounding the recess. It is noted that the expansion element may also be arranged so as to provide an outer surface being flush with the surface surrounding the expansion element.

In step S2, the nail with the smooth outer surface, formed by the nail shaft together with the expansion element, is inserted into a bone. For this, a bore is drilled through the hard corticalis to access the marrow channel within the bone. Further, the marrow channel may be prepared for receiving the nail by a reaming device.

In step S3, after the bone nail has reached a suitable position and orientation within the bone, screws are inserted through bores in the nail so as to fix fracture fragments relative to each other.

Finally, the position and orientation of the nail is stabilized within the bone by expanding the diameter of the nail, i.e. by adjusting the position and orientation of the expansion element relative to the nail shaft, substantially by moving the expansion element out of the recess.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practising the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

LIST OF REFERENCE SIGNS

10, 20 nail shaft
12, 22 recess
14, 24 threaded bore
16, 36 guiding means
30, 40 expansion element
42 connection
50 adjustment screw
60, 70 locking screw
80, 90, 100 nail
200 humerus
210 humerus head
d depth
l length
w width

The invention claimed is:

1. An intramedullary nail, comprising:
a nail shaft having a central longitudinal axis, an outer surface extending in a longitudinal direction and in a circumferential direction, wherein a recess is formed in the outer surface of the nail shaft, the recess having a length measured in the longitudinal direction, a width measured in a circumferential direction and a depth measured from the outer surface in a direction to the central longitudinal axis, the nail shaft defining a channel extending through the nail shaft transverse to the central longitudinal axis;

an expansion element having a shape and size adapted to be accommodated in the recess, the expansion element including a pin positionable within the channel of the nail shaft; and a first adjustment screw adapted to be accommodated in a first threaded bore extending through the nail shaft transverse to the central longitudinal axis, into the recess and partially into the expansion element, wherein the first adjustment screw is adapted to adjust a distance between the central longitudinal axis of the nail shaft and the expansion element.

2. The intramedullary nail of claim 1, further comprising a second threaded bore extending through the nail shaft and into the recess, and a second adjustment screw.

3. The intramedullary nail of claim 1, wherein the channel and the pin act in combination to guide an adjustment movement of the expansion element relative to the nail shaft.

4. The intramedullary nail of claim 1, wherein the length of the recess is between 10 mm and 40 mm.

5. The intramedullary nail of claim 4, wherein the length of the recess is between 20 mm and 25 mm.

6. The intramedullary nail of claim 1, wherein the width of the recess is between 1 mm and 8 mm.

7. The intramedullary nail of claim 6, wherein the width of the recess is between 2 mm and 5 mm.

8. The intramedullary nail of claim 1, wherein the depth of the recess is 2 mm or less.

9. The intramedullary nail of claim 8, wherein the depth of the recess is 1 mm or less.

10. The intramedullary nail of claim 1, wherein the shape and size of the expansion element is determined such that a contour of the outer surface of the nail shaft at the recess is completed by the expansion element, when the expansion element is accommodated in the recess.

11. The intramedullary nail of claim 1, wherein a cross section of the nail shaft at the recess is non-circular, perpendicular to the central longitudinal axis.

12. The intramedullary nail of claim 1, wherein the nail shaft has a proximal section and wherein the recess is formed in the proximal section.

13. A method of using the intramedullary nail of claim 1, comprising:

providing the nail shaft with the expansion element and the lateral recess, arranging the expansion element in the recess of the nail shaft so that the expansion element does not protrude beyond the outer surface of the nail shaft, inserting the nail shaft with the expansion element into the marrow channel of a bone, adjusting the distance of the expansion element to the nail shaft by operating the first adjustment screw so that the expansion element moves out of the recess.

* * * * *